United States Patent [19]
Dam et al.

[11] 4,217,642
[45] Aug. 12, 1980

[54] METHOD AND APPARATUS FOR LOCATING DATA CHARACTERIZING BLOOD FLOW THROUGH THE HEART

[75] Inventors: Naim G. Dam, Bayside; Thomas Picunko, Scarsdale, both of N.Y.; Henry H. Kramer, Moraga, Calif.

[73] Assignee: Bios Inc., Valhalla, N.Y.

[21] Appl. No.: 941,903

[22] Filed: Sep. 13, 1978

[51] Int. Cl.² ............................ A61B 5/02; G06F 3/14
[52] U.S. Cl. ................................ 364/416; 128/713; 340/709; 364/521
[58] Field of Search ............... 364/415, 416, 515, 518, 364/521; 340/709, 710, 712, 722; 128/2.05 R, 2.05 F, 2.05 V, 691, 713; 355/5

[56] References Cited
U.S. PATENT DOCUMENTS

| | | | |
|---|---|---|---|
| 3,911,419 | 10/1975 | Bates et al. | 340/709 |
| 3,996,925 | 12/1976 | Djordjevich | 364/416 |
| 4,020,391 | 1/1977 | Baxter | 340/709 |
| 4,060,713 | 11/1977 | Golay | 364/416 |
| 4,063,223 | 12/1977 | Schlig et al. | 340/709 |
| 4,118,695 | 10/1978 | Ogawa et al. | 340/709 |

Primary Examiner—Errol A. Krass
Attorney, Agent, or Firm—McAulay, Fields, Fisher, Goldstein & Nissen

[57] ABSTRACT

A method and improved apparatus for locating data of interest on a cathode ray tube display in a system for characterizing blood flow through the heart is disclosed. Apparatus comprising an adjustable cursor control circuit is utilized to generate a plurality of stable horizontal or vertical cursor lines on the cathode ray tube display thereby enhancing the user's ability to locate data of interest.

6 Claims, 10 Drawing Figures

METHOD AND APPARATUS FOR LOCATING DATA CHARACTERIZING BLOOD FLOW THROUGH THE HEART

BACKGROUND OF THE INVENTION

This invention relates to a method and improved apparatus for locating data of interest in conjunction with a diagnostic method of characterizing blood flow through the heart. More specifically, it relates to the use of an improved adjustable cursor control circuit for locating data of interest on a cathode ray tube display.

Conventional methods of locating data of interest on a cathode ray tube display such as the joystick, track ball and light pen, are generally limited to defining the x-y coordinates of a single point on the face of the cathode ray tube display. Generally, they do not have the capability to define a moveable cursor line on the face of the cathode ray tube display.

More sophisticated hybrid methods combining hardware and software techniques may be utilized to generate moveable cursor lines; however, many of these conventional systems utilize some form of analog to digital conversion which has an inherent instability of one-half the least significant bit (LSB). In the absence of corrective techniques this inherent instability usually appears as unwanted jitter on the cursor lines. In high resolution applications the effect of jitter is clearly undesirable.

An example of a high resolution system where the effect of jitter on the cursor lines is undesirable is illustrated in copending application Ser. No. 854,537, filed Nov. 25, 1977, entitled "Method and Apparatus for Characterizing Blood Flow through the Heart," assigned to the assignee of the present invention, and incorporated herein by reference. by providing the user with a stable method of locating data of interest on a cathode ray tube display the diagnosis and monitoring of patients is enhanced.

Accordingly, it is an object of the invention to provide a method for locating data of interest on a cathode ray tube display in conjunction with a diagnostic method of characterizing blood flow through the heart.

It is a further object of the invention to provide improved apparatus for locating data of interest on a cathode ray tube display in a system for characterizing blood flow through the heart.

It is still a further object of the invention to provide apparatus capable of generating a plurality of stable horizontal or vertical cursor lines to locate data of interest on a cathode ray tube display.

Another object of the invention is to provide a low cost adjustable cursor control circuit for locating data of interest on a cathode ray tube display.

SUMMARY OF THE INVENTION

The foregoing and other objects and advantages which will be apparent in the following detailed description of the preferred embodiment, or in the practice of the invention, are achieved by the invention disclosed herein, which generally may be characterized as a method and improved apparatus for locating data of interest on a cathode ray tube display, the method comprising the steps of:

(a) generating an interrogating cursor;
(b) driving said cursor with a digital counter;
(c) manually actuating a pulse train that is counted by said counter;
(d) positioning said cursor in any desired position on said display through said manual actuation;
(e) automatically interrogating the data that is intercepted by said cursor; and
(f) displaying in real time data and calculations developed from the coordinates of whatever data is being intercepted by said cursor;

and the apparatus comprising:

(a) means for generating an interrogating cursor;
(b) means for driving said cursor with a digital counter;
(c) means for manually actuating a pulse train that is counted by said counter;
(d) means for positioning said cursor in any desired position on said display through said manual actuation;
(e) means for automatically interrogating the data that is intercepted by said cursor; and
(f) means for displaying in real time data and calculations developed from the coordinates of whatever data is being intercepted by said cursor.

DETAILED DESCRIPTION OF PREFERRED EMBODIMENT

In order to afford a complete understanding of the invention and an appreciation of its advantages, a description of a preferred embodiment is presented below.

Figure 1:
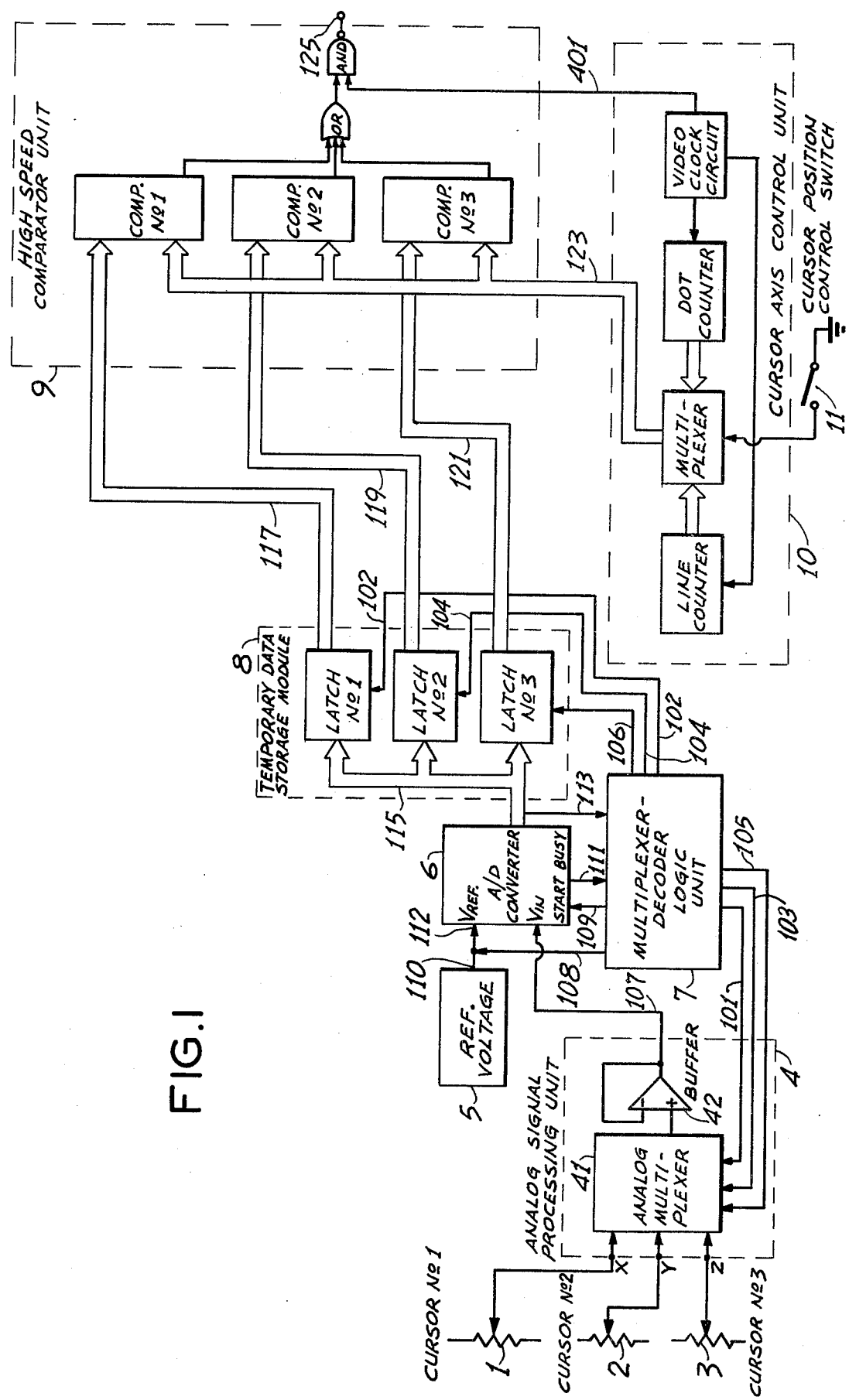
FIG. 1 is a block diagram of one embodiment of an adjustable cursor control circuit, in accordance with the present invention.

Referring now to FIG. 1, a block diagram of one embodiment of the adjustable cursor control circuit, in accordance with the present invention, is illustrated. As shown therein, the adjustable cursor control circuit consists of a number of functional subsystems comprising an analog signal processing unit 4, an analog to digital converter 6 controlled by a multiplexer-decoder logic unit 7, a temporary data storage module 8, a high speed comparator unit 9 and a cursor axis control unit 10.

For the sake of convenience the following discussion will be primarily limited to the generation of one moveable cursor line by the apparatus of the present invention. The operation of the other two cursor generators depicted in FIG. 1 is identical.

An analog signal of unknown amplitude is developed across a conventional potentiometer 1 and applied to the x input terminal of an analog signal processing unit 4. Control signal 101 generated in a multiplexer-decoder logic unit 7 allows the analog signal to pass through an analog multiplexer 41 in proper time and phase sequence, and through an operational amplifier 42 configured as a non-inverting buffer amplifier. The analog signal output 107 of the analog signal processing unit 4 is connected to the $V_{in}$ port of an analog to digital converter 6 consisting, for example, of Analog Devices Model 7570.

The analog to digital (A/D) conversion cycle is initiated by means of a start pulse 109 generated in the multiplexer-decoder logic unit 7.

Figure 2:
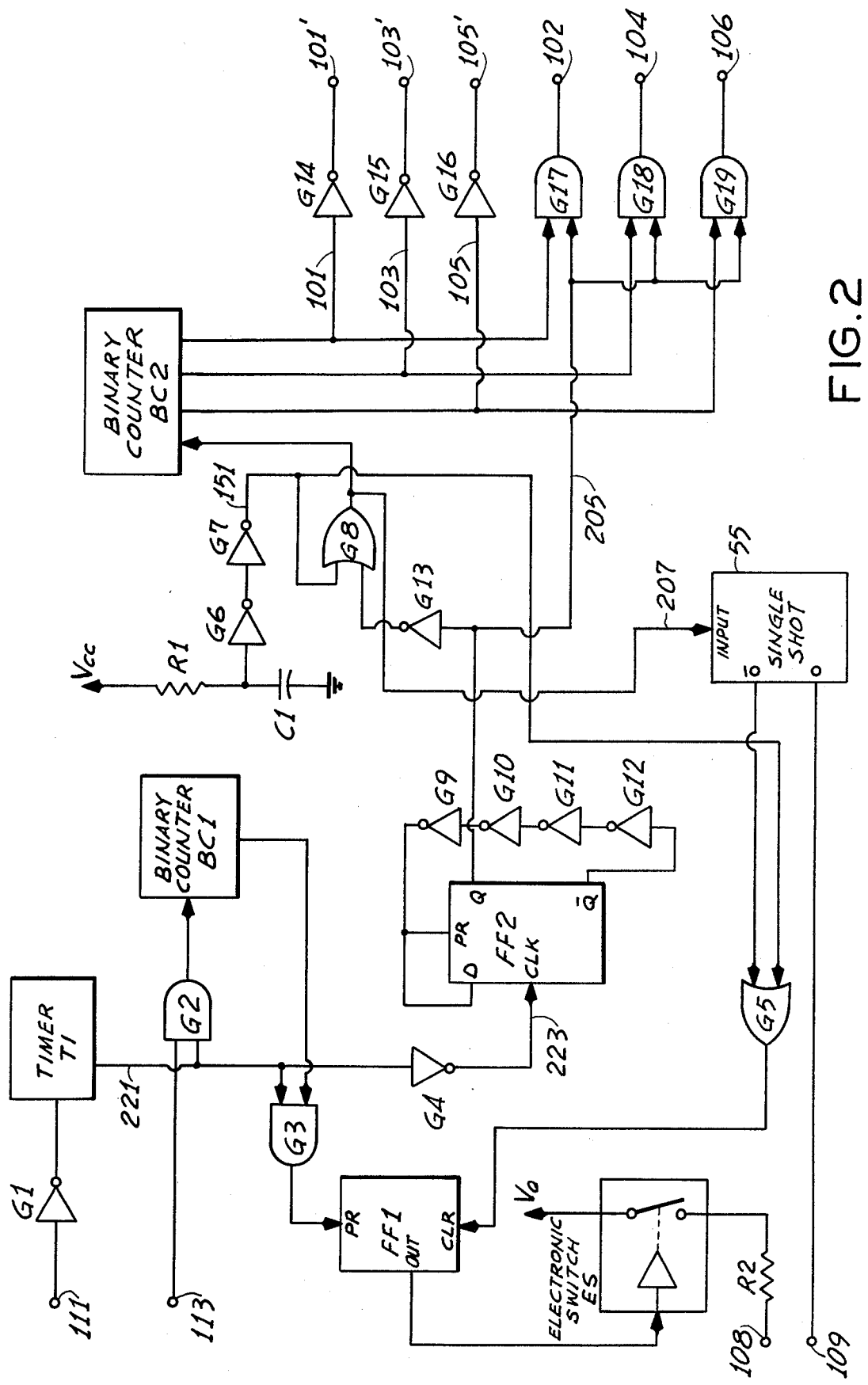
FIG. 2 is a schematic diagram of the multiplexer-decoder logic unit, in accordance with the present invention.

The technique of generating start pulse 109 is illustrated in FIG. 2. As shown therein, start pulse 109 is generated utilizing the power-on signal 151 created by the network consisting of gates G6 and G7. Power-on signal 151 fires single shot multivibrator 55. The $R_1C_1$ time constant is selected to provide a low level power-on signal to fire the single shot multivibrator 55.

Referring again to FIG. 1, after the A/D Conversion cycle has been initiated, the input analog signal 107 at $V_{in}$ port of A/D converter 6 is compared with a reference voltage 110 generated by a reference voltage source 5 consisting, for example, of Analog Devices Model 7501. Utilizing standard successive approximation techniques A/D converter 6 converts the input analog signal 107 to an 8 bit digital word 115.

The digital word output 115 of A/D converter 6 is stored in a conventional 8 bit register located in the temporary data storage module 8. The temporary data storage module comprises three latch registers each consisting, for example, of Texas Instruments Model 74273. The digital words corresponding to the analog signals developed across potentiometers 1, 2, and 3, respectively, are loaded in proper phase sequence, in each of the corresponding latch registers, by means appropriate strobe signals 102, 104 and 106 generated in the multiplexer-decoder logic unit 7.

Upon completion of the analog to digital conversion a busy signal 111 is generated within A/D converter 6. Busy signal 111 is transmitted to the multiplexer-decoder logic unit 7 where it is used to generate enabling signal 102. The enabling signal 102 is used to strobe the no. 1 latch register to store digital word 115.

The technique of generating enabling pulse 102 is depicted in FIG. 2. As shown therein, busy signal 111 starts timer T1 consisting of a conventional single shot multivibrator to generate signal 221. The timing period is preset in accordance with the user's requirements. At the expiration of the timing period a narrow pulse 205 is generated by flip-flop FF2 in conjunction with gates G9-G12. Pulse 205 is then gated with signal 101 through gate G17 to generate enabling pulse 102 which is used to strobe the no. 1 latch register to store digital word 115.

The timing of the circuitry depicted in FIG. 2 is such that the positive going edge of pulse 205 is used to store the digital word and the negative going edge of pulse 205 is used to advance binary counter BC2. At the same time, pulse 205 is used to generate start pulse 109 by means of a single shot multi-vibrator 55 in conjunction with gate G13.

Binary counter BC2 is a conventional programmable counter implemented as a divide by three counter. The counter advances to the next count on each negative going pulse. After three such pulses the counter is reset. In this manner signals, 101, 103 and 105 are generated in proper sequence, as are the corresponding enable signals 102, 104 and 106 used to strobe the latch registers.

Figure 3:
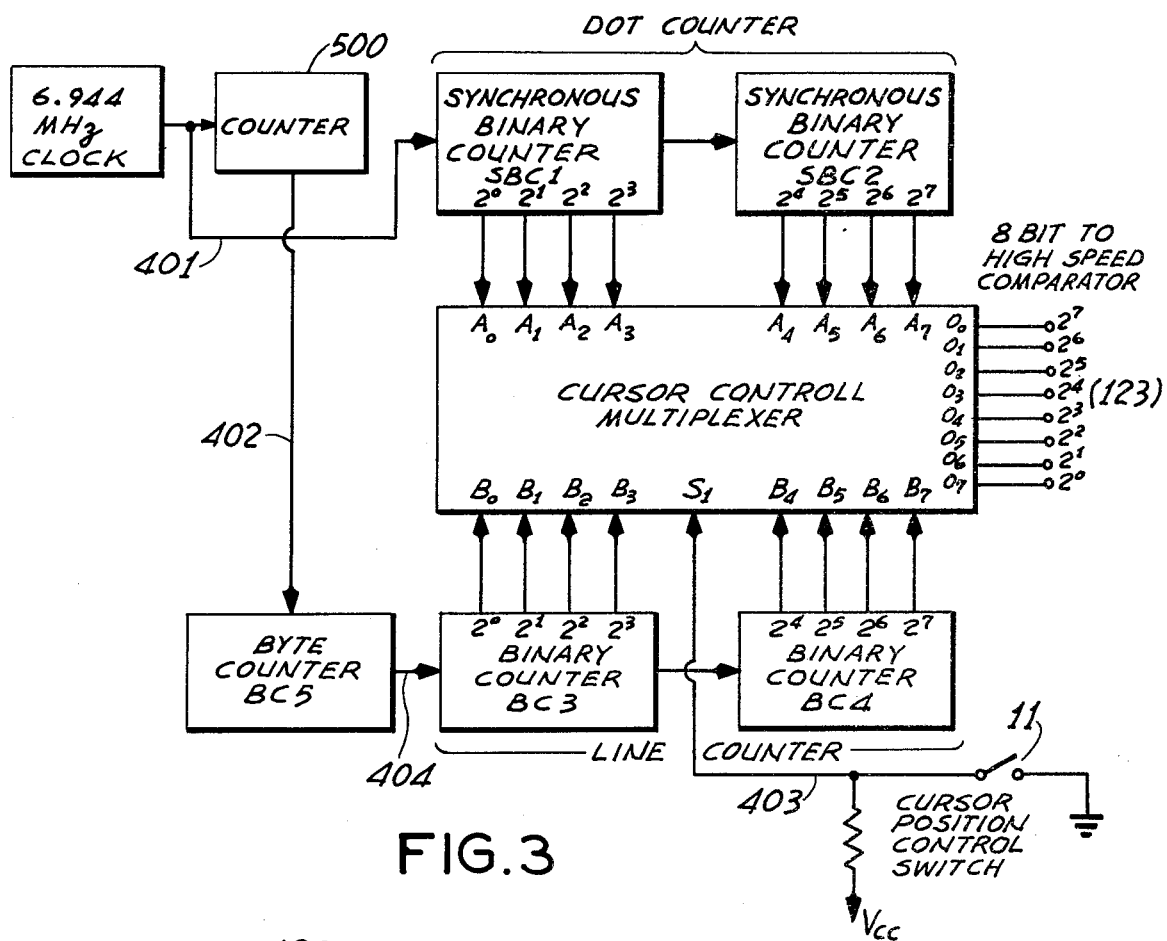
FIG. 3 is a block diagram of the cursor axis control unit.

Referring now to FIG. 3, the configuration of the cursor axis control unit 10 is depicted. As shown therein, a 6.944 MHz crystal controlled oscillator is used to provide a video clock pulse 401. Counter 500 is a conventional programmable counter arranged to count a preselected number of video clock pulses 401 per byte. In the embodiment depicted, counter 500 is programmed to generate an output pulse 402 for every eight video clock input pulses 401.

The dot counter consists of two conventional synchronous binary cascaded counters SBC1 and SBC2. It is clocked by video signal 401.

Initially, counters SBC1 and SBC2 are cleared. Thereafter, the first counter SBC1 begins to receive input video pulses 401. The second counter SBC2 receives one input pulse from the first counter SBC1 for every 16 ($2^4$) video clock pulses 401.

The outputs of the cascaded counters SBC1 and SBC2, $2^0$ through $2^7$, are connected to the input ports, $A_0$ through $A_7$, respectively, of the cursor control multiplexer.

Conventional byte counter BC5 receives input clock pulses 402 from counter 500. Byte counter BC5 generates one output clock pulse 404 for every 32 ($2^5$) input clock pulses 402. The byte counter output clock pulses 404 are transmitted to a line counter which consists of two conventional binary cascaded counters BC3 and BC4.

Initially, counters BC3 and BC4 are cleared. Thereafter, the first counter BC3 begins to receive input pulses 404 from the byte counter. The second counter BC4 receives one input pulse from the first counter BC3 for every 16 ($2^4$) output pulses 404 from the byte counter.

The outputs of the cascaded counters BC3 and BC4, $2^0$ through $2^7$, are connected to the input ports $B_0$ through $B_7$, respectively, of the cursor control multiplexer.

The cursor control multiplexer is a conventional eight pole two position electronic switch the position of which is determined by the digital logic level at the select input $S_1$. It may consist, for example, of an Intel Model 8255.

When the cursor position control switch 11 is in an open position, the signal at $S_1$ is at a logic one level and the cursor control multiplexer connects the inputs $A_0$ through $A_7$, from the dot counter, to the output ports $O_0$ through $O_7$, respectively, of the multiplexer. Similarly, when the cursor position control switch 11 is in a closed position, the signal at $S_1$ is at a logic zero level and the cursor control multiplexer connects the inputs $B_0$ through $B_7$, from the line counter, to the output ports $O_0$ through $O_7$, respectively, of the multiplexer.

In the particular embodiment being described, the face of the cathode ray tube display (not shown) is temporally divided into a matrix of 256×160 dots, i.e., it consists of 160 horizontal lines, each line comprising 256 dots.

The dot counter controls the timing and generation of the vertical cursors, and the line counter controls the timing and generation of the horizontal cursors.

Functionally, the dot counter counts 256 video pulses 401, corresponding to the number of dots comprising one horizontal line, and then resets itself. The byte counter generates one clock pulse for every 32 input clock pulses 402. This corresponds to the number of dots per horizontal line (32×8=256). The line counter, which is clocked by the output of the byte counter, counts 160 pulses 404, corresponding to the number of horizontal lines, and then resets itself.

Figure 4:
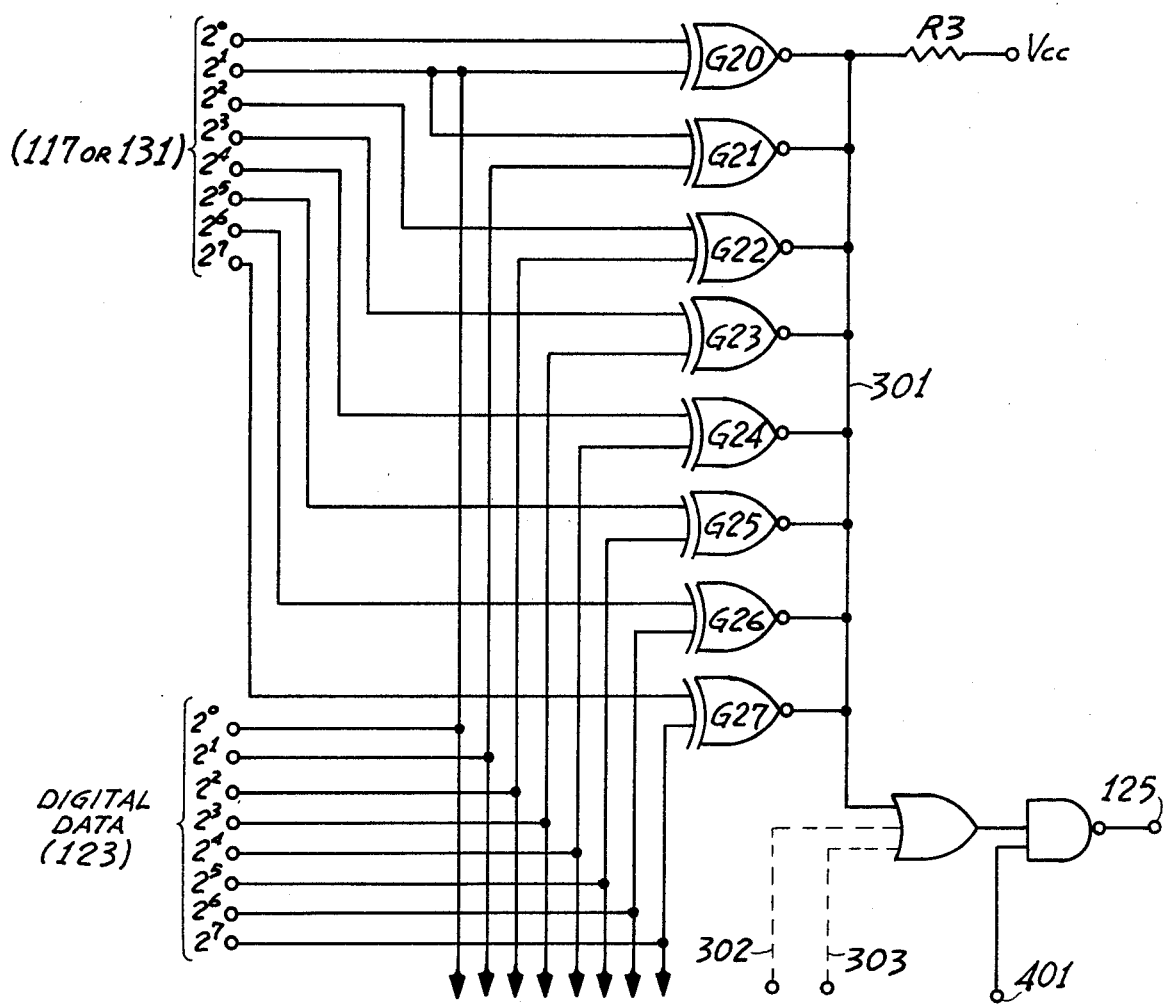
FIG. 4 is a schematic diagram of the high speed comparator circuit utilized in the adjustable cursor control circuit.

Referring now to FIG. 4, the configuration of one of the high speed comparators comprising high speed comparator unit 9 is depicted. As shown therein, the eight bit digital word 117 from the cursor control multiplexer, is compared with the eight bit digital word 123, from the temporary storage module 8. Typically, each of the high speed comparator circuits consists of standard exclusive nor gates. As configured, the comparator circuit is an equality comparator, i.e., it compares the digital word corresponding to one of the input analog voltages with the selected output of the cursor control multiplexer to detect equivalence. Depending upon user selection, the output of the cursor control multiplexer may be the contents of the dot counter, if the user desires a vertical cursor, or the contents of the line counter, if the user desires horizontal cursor. In either case, whenever the digital word corresponding to one of the input analog voltages is equivalent to the contents of the selected dot counter or line counter, a pulse 301 is generated which is gated with the video clock from the crystal controlled oscillator. The result is the generation of a video pulse 125 which appears as a single dot on the face of the cathode ray tube display. The series of dots formed as a result of the continuous operation of the dot counter or line counter generates either a vertical or horizontal cursor line. It should be apparent that changing the setting of one of the analog potentiometers changes the corresponding digital word stored in the temporary data storage module thereby causing the corresponding cursor line to change its position on the face of the cathode ray tube display.

Although the above description has been devoted primarily to the generation of a single moveable horizontal or vertical cursor line, it is possible to generate more than one line by continuously multiplexing the input analog voltages developed across two or more potentiometers. This is effected using multiplexer-decoder logic unit 7 in conjunction with analog multiplexer 41 in a manner similar to that previously discussed. In the embodiment illustrated in FIG. 1, three such potentiometers have been depicted, however, there is no reason why this number cannot be increased to accommodate a particular user's requirements.

Figure 5A:
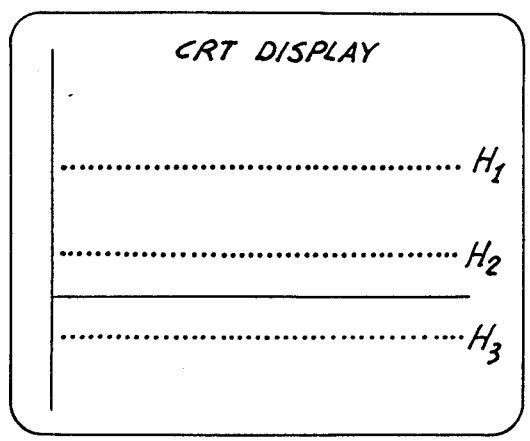
FIG. 5A illustrates a representative cathode ray tube display containing horizontal cursor lines.
Figure 5B:
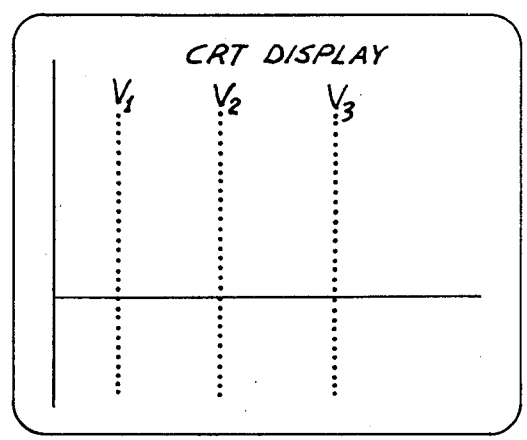
FIG. 5B illustrates a representative cathode ray tube display containing vertical cursor lines.

A representative cathode ray tube display 201 illustrating cursors generated in accordance with the present invention is depicted in FIGS. 5A and 5B. As shown therein, the user has the ability to generate up to three moveable horizontal cursors, $H_1$, $H_2$ and $H_3$, or three moveable vertical cursors, $V_1$, $V_2$ and $V_3$. As indicated previously, a particular cursor may be moved by changing the setting of the corresponding analog potentiometer.

Although the moveable cursors generated in accordance with the present invention, as described above, may be satisfactory for most applications, there may be some jitter on the cursor lines as a result of the analog to digital conversion process. For high resolution applications the jitter effect on the cursor lines may not be tolerable. Accordingly, a unique technique for removing the jitter associated with the analog to digital conversion process has been devised, as described below.

Referring again to FIG. 1, a feedback hysteresis loop implemented within the multiplexer-decoder logic unit 7 is used to modify reference signal 110 used by A/D converter 6 to effect the analog to digital conversion.

The details of the feedback hysteresis circuitry are depicted in FIG. 2. As shown therein, a power on condition causes flip-flop FF1 to reset, thereby opening the conventional analog electronic switch ES. This in turn results in a binary zero signal at output 108. At the end of the analog to digital conversion cycle, timer T1 is activated and generates signal 221. The least significant bit (LSB) 113 of the digital output of the A/D converter is gated with signal 221 by means of gate G2. The output of gate G2 is connected to programmable binary counter BC1 which is programmed to check the signal jitter on LSB line 113. The output of BC1 is gated with signal 221 by means of gate G3.

As indicated above, at the end of the A/D conversion cycle, the LSB line 113 generally is not stable, i.e., it flickers from a low level to a high level intermittently due to noise fluctuations of the analog input signal. Binary Counter BC1 counts the number of changes in the state of LSB line 113 over a predetermined period of time set by the timer output signal 221. If the number of such changes exceeds an arbitrary preset number, then binary counter BC1 generates a pulse which is gated through gate G3 and sets flip-flop FF1. This causes the output of flip-flop FF1 to switch to a high level thereby causing analog electronic switch ES to close. This causes a positive or negative voltage, depending on user selection, to be connected to resistor R2.

When electronic switch ES is closed, the resulting current flowing through resistor R2 flows substantially through the internal impedance of reference voltage source 5. The resulting voltage drop across the internal impedance causes the output reference voltage 110 to increase or decrease by a fixed amount depending on the polarity of $V_0$. The value of resistor R2 is selected such that the voltage drop across the internal impedance of reference voltage source 5 is equal to $$\tfrac{1}{2} \times \frac{\text{output reference voltage (110)}}{2^n}$$

where n is the number of bits in the A/D conversion.

To further illustrate the significance of the hysteresis loop described above in removing the jitter on the cursor lines, the following discussion, in conjunction with FIGS. 1 and 2, may be helpful.

Generally, in an 8 bit analog to digital conversion, the lowest analog input voltage, usually zero volts, is assigned the digital value 0000 0000 and the highest analog input voltage is assigned the digital value 1111 1111. Between these two extremes the analog input voltage is converted to a binary number that is the nearest integer to $$\frac{V_{in}}{V_{ref}} \times 2^n,$$

where
  $V_{in}$: analog input voltage from the cursor potentiometer;
  $V_{ref}$: reference input to the A/D converter; and
  n: number of bits in the A/D conversion.

The modified signal 112 is composed of reference signal 110 and feedback signal 108. When switch ES is open feedback loop 108 is open and signal 110 represents the reference input 112 to the A/D converter 6.

If the analog input signal 107 from the cursor potentiometer is $V_{fs}/2$, where $V_{fs}$=full scale signal level and the value of the signal is equal to $V_{ref}$, then the unknown analog signal 107 is $V_{fs}(/2-1$ LSB) the corresponding digital value is 0111 1111 and LSB line 113 is stable and no jitter occurs on the cursor lines. If the analog input signal 107 is $V_{fs}(/2-\frac{1}{2}$ LSB), the corresponding digital value flickers between 1000 0000 and 0111 1111. This causes LSB line 113 to flicker between a low level (0) and a high level (1) causing jitter on the cursor lines. As previously explained, the hysteresis feedback loop modifies the reference signal 110. The modified signal 112, which is composed of $V_{ref}\pm\frac{1}{2}$ LSB Value of the $V_{ref}$, eliminates the flicker of LSB line 113 between a low level (0) and a high level (1). The digital value corresponds to a new stable value of 0111 1111 or 1000 0000, depending on the polarity of the feedback signal 108.

Referring again to FIG. 1, signal 112, modified in accordance with the technique described abive, is transmitted to the $V_{ref}$ input of the A/D converter 6. From this point the rest of the system works as described previously, however, the effect of jitter on the cursor lines has been substantially reduced.

Figure 6:
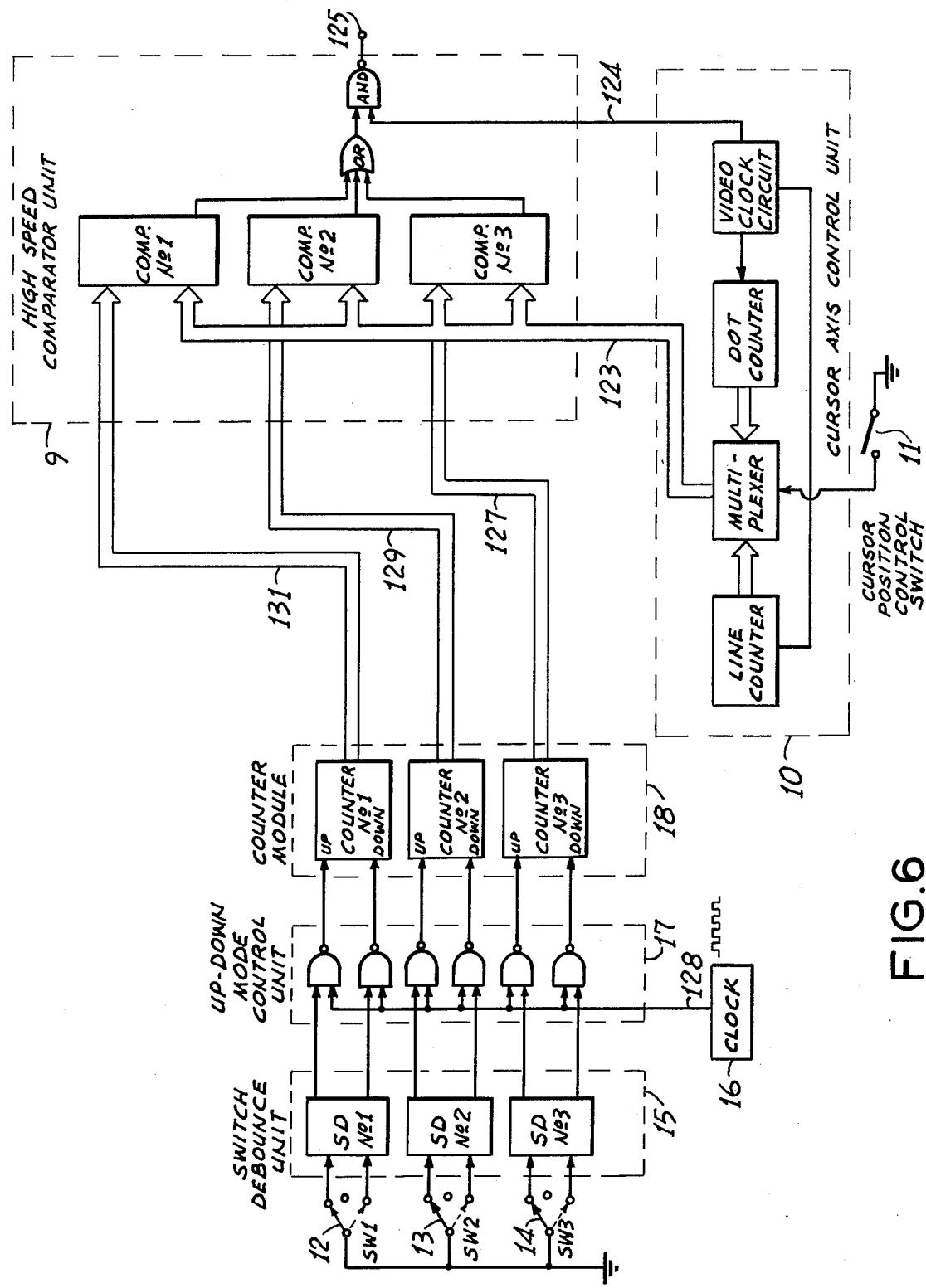
FIG. 6 is a block diagram of an alternate embodiment of an adjustable cursor control circuit, in accordance with the present invention.

An alternate embodiment of the present invention, designed to improve the performance at a substantial cost reduction, is depicted in FIG. 6. As shown therein the A/D conversion technique has been replaced by a digital counter approach. The specifics of the switch debounce unit 15, up-down mode control unit 17 and the counter module 18 are illustrated in greater detail in FIG. 7.

Figure 7:
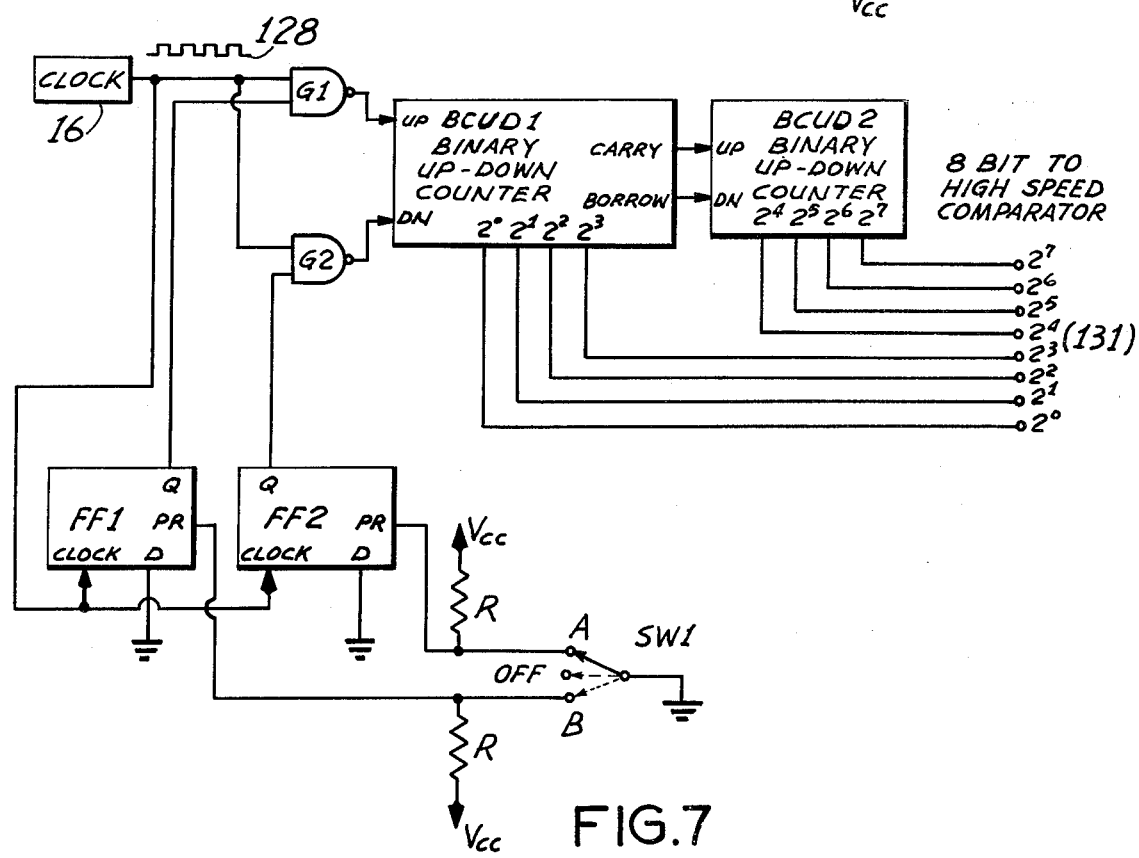
FIG. 7 is a block diagram of the digital counter utilized in the alternate embodiment of the present invention.

Referring now to FIG. 7, a clock 128, generated by conventional means 16, is used to gate the outputs of flip-flop FF1 and flip-flop FF2 through gates G1 and G2, respectively. The output of gate G1 is applied to the Up input of cascaded binary up-down counters BCUD1 and BCUD2 and the output of Gate G2 is applied to the Down input of the cascaded binary up-down counters. As connected BCUD1 and BCUD2 from an eight bit counter.

When switch SW1 is in the off position, the leading edge of the first clock pulse 128 resets the outputs of flip-flops FF1 and FF2 to a low state. The resulting low level signal from FF1 and FF2 inhibits the transmission of clock pulses 128 through gates G1 and G2.

When switch SW1 is in the R position, a low level signal is applied to the preset (PR) port of flip-flop FF1. Flip-Flop FF1 also performs the function of switch debounce. This causes the output of FF1 to switch to a high level, thereby allowing the clock pulses 128 to be transmitted to counter BCUD1 through Gate G1. Similarly, when the switch SW1 is in the L position, a low level signal is applied to the preset (PR) port of FF2. This causes the output of FF2 to switch to a high level, thereby allowing the clock pulses 128 to be transmitted to counter BCUD1 through Gate G2.

Starting with counters BCUD1 and BCUD2 cleared, and the switch SW1 in the R position, clock pulses 128 enter counter BCUD1 through Gate G1. After every 16 ($2^4$) clock pulses, counter BCUD1 generates a pulse which is transmitted to counter BCUD2. The outputs of counters BCUD1 and BCUD2, $2^0$ through $2^7$, are fed to the high speed comparator circuit. As discussed above, the comparator circuit is an equality comparator consisting of gates G20–G27.

Referring again to FIG. 4, the comparator circuitry compares the eight bit data word 131 stored in counters BCUD1 and BCUD2 with the output 123 of the cursor axis control unit 10. As discussed above, the output 123 of the cursor axis control unit may be the contents of the dot counter or the line counter, depending upon the user's application. The comparator circuitry generates a pulse when the eight bit data word 131 equals the output 123 of the cursor axis control unit. The output pulse 301 is then gated with the video clock 401 to generate video pulse 125 which appears as a single dot on the face of the cathode ray tube display. The series of dots formed results in either a horizontal or a vertical cursor line, depending on the user's selection.

The position, A or B, of switch SW1 controls the position of a moveable line on the cathode ray tube display. When held in the desired position by the user, the cursor moves across the face of the cathode ray tube display for as long as the switch is held in said position. For example, when using a vertical cursor, switch position B causes counters BCUD1 and BCUD2 to increment, thereby resulting in a movement of the cursor to the right from its previous position. Similarly, switch position A causes counters BCUD1 and BCUD2 to decrement, thereby resulting in a movement of the cursor to the left from its previous position.

An output of BCUD1 and BCUD2 of, for example, 0000 1000 represents a cursor position on the cathode ray tube display at the eighth line from the zero reference. Setting switch SW1 in position B allows counter BCUD1 and BCUD2 to increment from 0000 1000 to a new value up to 1111 1111, corresponding to a new cursor position to the right of the previous position represented by 0000 1000.

Similarly, placing switch SW1 in position A allows the counter to decrement to a new value down to 0000 0000, corresponding to a new cursor position to the left of the previous position represented by 0000 1000.

Similarly, when using a horizontal cursor, switch position A causes a downward movement and switch position B causes an upward movement of the cursor.

The counter technique utilized in the alternate embodiment described above also avoids jitter on the cursor line, since it does not utilize an analog to digital conversion technique which is the source of the jitter.

In both of the embodiments described above, the generation of a single dot, corresponding to a given video pulse 125, on the face of the cathode ray tube display is performed by conventional interfacing techniques described more fully in copending application Ser. No. 854,537.

The adjustable cursor control circuit may be used to automatically interrogate a data set displayed on the field of a cathode ray tube either in a vertical or horizontal mode as depicted in FIGS. 5A and 5B. When the cursor control switch (SW1, FIG. 7) is activated, the cursor's location on the data display moves in one direction or the other depending on the polarity of the switch activation. For example, the cursor can be made to move at a constant rate across the display in a rightward or a leftward direction corresponding to a rightward or leftward switch movement. The cursor in this method will intercept continuously various portions of the displayed data in discrete stepwise time intervals. A digital calculating means can interrogate the portion of the cursor either while it is in motion or stationary, and continuously update digital calculations associated with the data at that cursor position, displaying the results in real time on the cathode ray tube. Thus, the user is able to locate the data of interest of blood flow through the heart and determine automatically in real time inportant characteristics of the magnitude or the value of this data.

Figure 8:
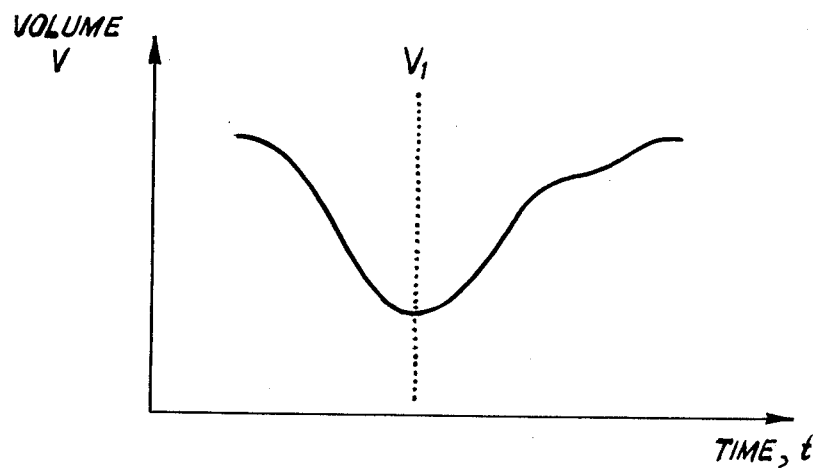
FIG. 8 illustrates a representative use of a vertical cursor line to locate a specific data point.
Figure 9:
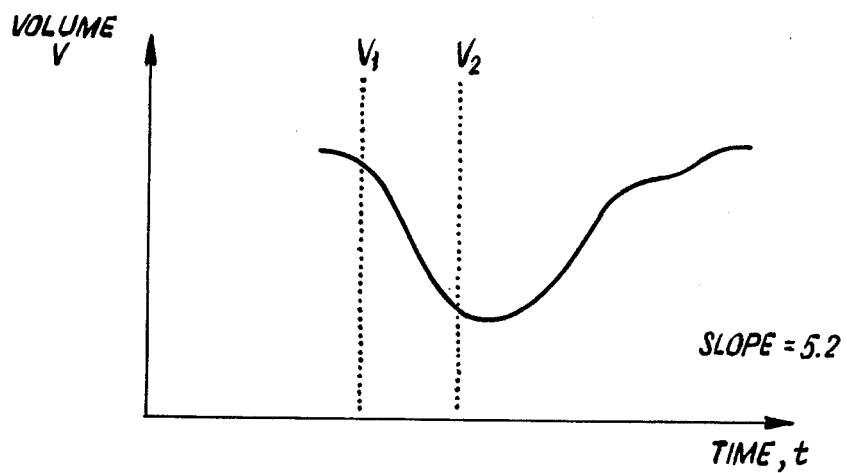
FIG. 9 illustrates a representative use of two vertical cursor lines to scan data on the cathode ray tube display.

Referring to FIGS. 8 and 9, it is apparent that this method of interrogating blood flow data is useful to the physician in his measurement of key parameters of heart performance, and the rapidly changing cursor location enables him to determine the proper location of specific data points: for example, the minimum of the curve shown in FIG. 8. Through the use of the cursor, the physician is also able rapidly to verify the correctness of the blood flow measurements through his selection of a data point and its corresponding calculation and display in real time.

The use of multiple cursors as shown in FIG. 9 also enables a method of detecting the optimal level of heart blood flow parameters. As shown therein, two cursors moving in the same direction a discrete distance apart may be used to scan the display data of the cathode ray tube. In this method of operation, the parameter of interest, e.g., the slope of the displayed data between the two cursors, is calculated and displayed on the cathode ray tube in real time. The physician simple drives continuously the cursor location across the display to determine the flow and position of the maximum slope of the curve or any other optimal location.

It is clear that the above description of the preferred embodiment in no way limits the scope of the present invention which is defined by the following claims.

What is claimed is:

1. The method of examining data concerning characteristics of the blood flowing through a heart comprising the steps of:
   displaying a curve representing blood flow measurements as a function of time on a display tube,
   generating at least one interrogating cursor line,
   manually actuating a pulse train,
   driving said cursor line with said pulse train,
   positioning said cursor at a selected location on said display through said manual actuation,
   automatically interrogating said curve where intercepted by said cursor, when said cursor is positioned at said selected location, to provide data,
   computing the value of a predetermined parameter of a patient's blood flow from said data, and
   displaying said computed value of said predetermined parameter substantially simultaneous with the interrogation of said curve.

2. The method of claim 1 further comprising the steps of:
   repeating said steps of positioning, interrogating, computing and displaying at a number of selected positions on said display to thereby locate an optimum value of said predetermined parameter.

3. The method of examining data concerning characteristics of blood flowing through a heart comprising the steps of:
   displaying a curve representing blood flow measurements as a function of time on a display tube,
   generating a plurality of interrogating cursor lines,
   driving each of said cursor lines with a separate pulse train, each of said pulse trains being separately manually actuated,
   positioning each of said plurality of cursor lines at selected locations on said display,
   automatically interrogating said curve where intercepted by each of said cursors positioned at said selected locations to provide data,
   computing the value of a predetermined parameter of a patient's blood flow from said data, and
   displaying said computed value of a predetermined parameter substantially simultaneous with the interrogation of said curve.

4. The method of claim 3 further comprising the steps of:
   repeating said steps of positioning, interrogating, computing and displaying at a number of selected positions on said display to thereby locate an optimum value of said predetermined parameter.

5. Apparatus for locating and examining data characterizing blood flow through a heart comprising:
   a display tube,
   means for displaying a curve representing blood flow measurement as a function of time on the face of said display tube,
   a manually actuated switch having an on state and an off state, said switch when in said on state generating a predetermined pulse train,
   means for generating an interrogating cursor line on the face of said display tube,
   means for driving said cursor line with said predetermined pulse train thereby positioning said cursor line with said manually actuated switch,
   means for interrogating said curve at selected positions where intercepted by said cursor line to provide data,
   means for computing the value of a predetermined parameter of a patient's blood flow from said data, and
   means for displaying said computed value of said predetermined parameter substantially simultaneous with the interrogation of said curve.

6. Apparatus for locating and examining data characterizing blood flow through the heart comprising:
   a display tube,
   means for displaying a curve representing blood flow measurements as a function of time on the face of said display tube,
   means for generating a plurality of interrogating cursor lines on the face of said display tube,
   a plurality of manually actuated switches,
   each of said switches when actuated generating a predetermined pulse train,
   means for driving each of said cursor lines with a separate one of said pulse trains to independently position each of said plurality of cursor lines in any selected position on said display through independent manual operation of said switches,
   means for interrogating said curve at said selected positions where intercepted by said cursor lines to provide data,
   means for computing the value of a predetermined parameter of a patient's blood flow from said data, and
   means for displaying said computed value of said predetermined parameter substantially simultaneous with the interrogation of said curve.

* * * * *